(12) United States Patent
Goldman et al.

(10) Patent No.: US 8,198,512 B2
(45) Date of Patent: Jun. 12, 2012

(54) HIGH PIGMENT GOLDEN BEETS

(75) Inventors: Irwin L. Goldman, Madison, WI (US); Dwight N. Breitbach, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1246 days.

(21) Appl. No.: 11/358,507

(22) Filed: Feb. 21, 2006

(65) Prior Publication Data

US 2006/0212968 A1     Sep. 21, 2006

Related U.S. Application Data

(60) Provisional application No. 60/657,146, filed on Feb. 28, 2005, provisional application No. 60/673,092, filed on Apr. 20, 2005.

(51) Int. Cl.
| | |
|---|---|
| *A01H 5/00* | (2006.01) |
| *A01H 5/10* | (2006.01) |
| *A01H 5/12* | (2006.01) |
| *A01H 5/06* | (2006.01) |
| *A01H 1/02* | (2006.01) |

(52) U.S. Cl. ........................................ 800/295; 800/260
(58) Field of Classification Search .................. 800/298, 800/295

See application file for complete search history.

(56) References Cited

U.S. PATENT DOCUMENTS 6,353,156 B1 * 3/2002 Gabelman et al. ............ 800/298

OTHER PUBLICATIONS

Gaertner et al. 2003. HortScience 38(5): 804.*
Gaertner et al. 2005. J. Amer. Soc. Hort. Sci. 130(3): 424-433.*
Gaertner et al. HortScience 38(5): 804, 2003.*
Nilsson. 1973. Swed J Agr Res 3: 187-200.*
Nilson, T., "The Pigment content in Beetroot with Regard to Cultivar, Growth, Development and Growing Conditions," Swedish J. Agric. Res. 3:187-200 (1973).
Watson, J.F., et al., "Genetic Analysis of Betacyanine, Betaxanthine, and Sucrose Concentrations in Roots of Table Beet," J. Amer. Soc. Hort. Sci. 109:386-391 (1984).
Wolyn, D.J., et al., "Selection for Betalain Pigment Concentrations and Total Dissolved Solids in Red Table Beets," J. Amer. Soc. Hort. Sci. 115:165-169 (1990).
Nilsson, T. 1973. The pigment content in beetroot with regard to cultivar, growth, development and growing conditions. Swed. J. Agr. Res. 3:187-200.
Watson, J.F. and W.H. Gabelman. 1984. Genetic analysis of betacyanin, betaxanthine, and sucrose concentrations in roots of table beet. J. Am. Soc. Hort. Sci.109:386-391.
Wolyn, D.J. and W.H. Gabelman. 1990. Selection for betalain pigment concentrations and total dissolved solids in red table beets. J. Amer. Soc. Hort. Sci. 115:165-169.

* cited by examiner

*Primary Examiner* — Anne Grunberg
*Assistant Examiner* — Keith Robinson
(74) *Attorney, Agent, or Firm* — Quarles & Brady LLP

(57) ABSTRACT

A method for the creation of high pigment yellow or golden beets is described. High pigment yellow beets have enhanced levels of betaxanthins while limiting the abundance of betacyanins so that the beets themselves are yellow. The beets are useful as a table food having enhanced nutritional value because of the enhanced pigment concentration and also as a source of pigment itself.

9 Claims, 1 Drawing Sheet

HIGH PIGMENT GOLDEN BEETS

CROSS-REFERENCE TO RELATED APPLICATIONS

This application claims priority from U.S. Provisional patent application Ser. No. 60/657,146 filed Feb. 28, 2005 and Ser. No. 60/673,092 filed Apr. 20, 2005.

STATEMENT REGARDING FEDERALLY FUNDED RESEARCH OR DEVELOPMENT

None.

BACKGROUND OF THE INVENTION

Among the common table vegetables available for human consumption is the table beet. Beets are part of the diet of many people. While there has been some development of new varieties of beet, the genetic potential of table beets, both in variety and production, is not close to being fully explored.

Another trend in modern vegetable development is the creation of varieties of plants which have enhanced concentrations of natural plant metabolites. This is done for two reasons. One reason is to make eating vegetables of increased nutritional value. The other reason is to use the vegetable as a mechanism to produce the metabolite in useful quantities so that the can be extracted for nutritive purposes, for additives to other foods, or potentially even for therapeutic or prophylactic purposes. Among the plant metabolites which are attractive for enhancement are pigment molecules, many of which are also associated with the dietary benefits that humans receive when eating pigmented vegetables.

Table beets are generally available in the United States in two colors, red and golden. The color of beets is determined by a class of pigment molecules known as betalains. Betalains are water-soluble, vacuolar pigments produced by select fungi and plants within select families of the Order Caryophyllales, including the table beet (Beta vulgaris subsp. vulgaris). Betalains can be differentiated from anthocyanins by their nitrogenous composition and biosynthesis. Betalains and anthocyanins have a mutually exclusive production in plants. Plants that produce betalains do not produce anthocyanins and vice versa. Anthocyanins arise from a condensation between three malonyl-CoA molecules while betalains are created from the condensation of a primary or secondary amine (cyclodopa glucoside or 4,5-secodopa) with betalamic acid resulting in the structure of a 1,2,4,7,7-pentasubstituted 1,7-diasaheptamiethin system.

Betalains are classified into two major pigment groups: betacyanins (BC) and betaxanthins (BX). Betacyanins are produced from a condensation of betalamic acid with cyclodopa while betaxanthins result from a condensation reaction of betalamic acid with specific amino acids. Betacyanins (Amax 540 nm) produce a red-violet hue; betaxanthins (Amax 480 nm) produce a yellow hue. The betacyanins differ from the betaxanthins by the conjugation of a substituted aromatic nucleus to the 1,7-diasaheptamethinium chromophore, which is present in betacyanins. The ratio of the two pigments contributes to the final color of the plant tissue. Beets in which the concentration of betacyanins is high enough appear red in color, the red color produced by the betacyanins masking the concentration of betaxanthins.

While there is significant variation in pigment content in beet genotypes, in commercial beet varieties currently on the market, betaxanthins constitute only 20-30% of the total pigments contents of the beets. Efforts have been made before to produce beets which have enhanced levels of betacyanins. U.S. Pat. No. 6,353,156 describes a high pigment red table beet with enhanced levels of betacyanins produced in its tissues. Those beets were bred for generalized high pigment levels, and being red beets, produce enhanced levels of both betacyanins and betaxanthins.

Significant effort has been made in recent years to improve the nutritional content of table foods by increasing the amounts of metabolites in the food thought to be of nutritional importance. Betalains are one such metabolite, being thought to be significant antioxidants. However, no presently commercially availably beet varieties are high in betaxanthins without concurrent high concentrations of betacyanins. While there is one commercial variety of yellow table beet currently sold for cultivation in the U.S., known as Burpee's Golden, and some essentially derived cultivars, the variety and the cultivars do not have high levels of betaxanthins, the yellow color being simply a reduction in total pigment in the variety. The cultivars also tend to have poor seed quality. There are no commercial varieties of golden beet with high levels of betaxanthins.

SUMMARY OF THE INVENTION

The present invention is summarized in a beet plant which is yellow in color and which contains in excess of 100 mg of betaxanthins per 100 grams fresh weight of the root, the root having less betacyanin content than its betaxanthin content It is an object of the present invention to provide a variety of golden table beets with high levels of betaxanthins, useful both as table food and as a source of pigment production for yellow pigment.

It is a feature of the present invention that it provides a food source with enhanced nutritional value.

Other objects, features and advantages of the present invention will become apparent from the following specification.

DETAILED DESCRIPTION OF THE INVENTION

Figure 1:
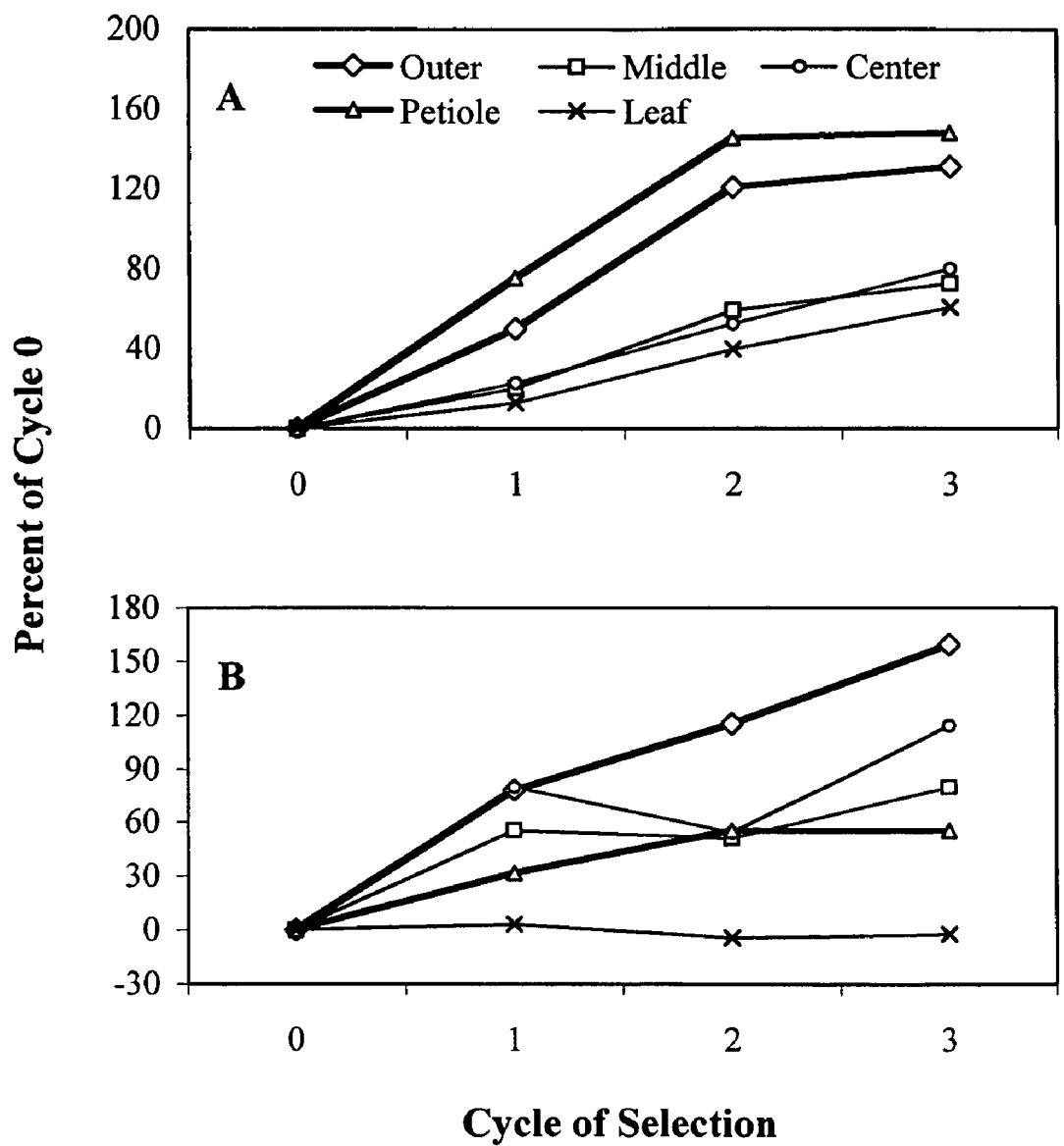
FIG. 1 is a graphical representation of some of the data from the examples described below.

The present invention is intended to enable the cultivation and consumption of yellow or golden beets. The plants described here are believed to be the first variety of golden beet with enhanced levels of betaxanthins occurring in the beets. The plants are useful for enhanced nutrition table food as well as a source of betaxanthins for use as pigments or for other purposes.

The breeding effort for the golden beet line began with beets produced in an earlier red beet breeding program intended to produce beets having high levels of betalains in general and either high or low accompanying solids. This breeding effort is described in previously mentioned U.S. Pat. No. 6,353,156, the disclosure of which is hereby incorporated by reference. Overlapping in time with the red beet breeding effort described in that patent, a parallel breeding program was begun to increase the betaxanthin levels in yellow table beet. In general, the strategy followed a similar plan as with the red beets, except that the total dissolved solids was neither selected for nor against. The sole criterion used in the breeding program was selection for high pigment level, i.e. betaxanthin concentration. Recurrent selection has resulted in over 250% increase in betaxanthin concentration between C0-C4 for the yellow table beet lines.

The nomenclature for beet breeding lines can be confusing. Beets have a self-incompatibility trait and hence must always be open-pollinated from maintenance lines. This being true, the strict definitions of plant varieties applicable to self-pollinated inbred plant varieties are not useful for beet. For purposes of this specification, the beet lines described here may be thought of as evolving into a variety or into a closely inbred population, the difference not being relevant. What is important is that it is taught here that yellow, or golden, beets can be bred which have enhanced levels of betaxanthins with a betacyanins concentration that permits the beets to remain visibly yellow rather than red. All prior high pigment beets were red.

Phenotypic selection in this breeding program was based upon the pigment concentration of cylindrical core samples (2 cm length by 18 mm in diameter) taken from the outer 2 cm of root tissue. Pigment concentration is obtained from a bulked sample of ten individuals per half-sibling family. Therefore, selection for pigment in the yellow table beet recurrent selection programs is based solely on the pigment concentration of the outer 2 cm zone of the root, rather than the pigment concentration throughout the entire beet root. Observations had earlier suggested that pigment levels in the outer zone of high pigment beets were significantly higher than those in the internal layers. The objectives of this study were to determine the spatial distribution of pigment and total dissolved solids (TDS) throughout root, leaf and petiole tissue of selected populations from the yellow recurrent selection programs.

To make other new populations or lines of high pigment golden beets, two methods are possible from here. One method is to reproduce the breeding and selection scheme described here to make other populations which share the same high pigment characteristics. The data presented here makes it clear that this can be done. The other method is to use the deposited plant material described here as a starter material for the breeding of high pigment golden beets.

EXAMPLES

Plant material and experimental design. A comprehensive list of all table beet populations used in the development of both red and yellow high pigment beets is presented in Table 1. Table 1 shows the red and yellow beet populations and lines grown at Arlington, Wis. since 2002 and evaluated for distribution of pigment concentration and dissolved solids. Cycles 2, 4, 8, 9, 12 (both HPHS (high pigment high solids) and HPLS (high pigment low solids) populations) and cycles 13 and 15 (defined as the Ruby Lake population) were chosen from the red table beet program. Cycles were chosen to represent the different categories of selection used throughout the red table beet selection program. Individual cycles within the selection categories were chosen based on a seed germination test. Cycles 0-3 were chosen from the yellow table beet program. Bulked seed stocks were created for each cycle by combining equal volumes of seed from every half-sib family within the selected cycle. Checks consisted of one F1 hybrid 'Big Red' for red table beets and one open-pollinated population 'Golden Boy' for yellow table beet populations. 'Big Red' and 'Golden Boy' are the standard checks used in the red and yellow table beet recurrent selection programs.

Experiments were conducted in 2002 at The Arlington Horticultural Research Farm (Arlington, Wis.) in plano silt loam soil. Experiments were conducted in two environments, consisting of an early and late planting. Eighteen beet entries (Table 1) were planted in two environments which represented two planting dates (7 May and 21 June). These experiments were harvested at two dates (8 August and 10 September). Plots were arranged in a split-plot design with 4 randomized complete blocks of entries as main plots. Tissue zones represented sub-plots within populations. Plots consisted of single rows (3.66 m long and 46 cm apart) of all populations and checks. Each main plot was surrounded on two sides by two guard rows composed of one row of 'Big Red' and one row of 'Croni'. Each experiment was treated separately in the analysis of variance.

Ten randomly chosen roots from each row were harvested and topped by hand. Roots were washed, air-dried and weighed before sampling. Shoots and roots were stored at 4° C. until sampling. All tissues were sampled within 48 hours of harvesting. Tops were sampled by separating petiole from leaf tissue at the base of the leaf. Root samples consisted of tissue cylinders obtained from the thickest portion of longitudinally-halved roots with a core borer. The average beet diameter was ~6 cm. Cylinders for TDS and pigment analysis were 9 cm and 18 cm diameter, respectively. Cylinders were then divided into equal sections (~1 cm thick) representing the outer, middle and center zone of the root, resulting in 20 subsamples per zone per row. The samples were then stored in plastic bags at −20° C. until analyses were performed.

Pigment analysis. Pigment analyses followed the method of Wolyn and Gabelman (1990) with modifications. Frozen samples for pigment analysis were ground using a standard food processor and then were combined with distilled water equal to 200% of the sample weight. The mixture was homogenized for 2 min using an industrial blender (Waring Co.) and a 15-mL aliquot was removed. Aliquots were centrifuged (31,700 g) for 30 min at 4(C. A 25 µL aliquot of the root extract supernatant (200 µL for leaf and petiole extracts) was diluted in 4 mL of distilled water. The absorbance of the solution was measured at 476, 538 and 600 nm. Betacyanin and betaxanthin levels were computed as mg pigment·100 g$^{-1}$ fw according to the method of Nilsson (1973). The betacyanin/betaxanthin ratio (BC:BX) was calculated as a separate variable.

Total solid analysis. Total dissolved solids (TDS) analysis followed the method of Wolyn and Gabelman (1990). Frozen samples were thawed to room temperature and hand-pressed within sealed plastic bags to produce fresh juice. 30 μl of juice were analyzed with a refractometer (Fisher-Scientific Instruments) to determine percent TDS.

Statistical analysis. Data were initially screened for normality using the Shapiro-Wilks test (P>0.05). BC and BX values for all tissue types in both red and yellow populations were transformed using either an exponential or logarithmic scale. Normalized data were subjected to an analysis of variance using the generalized linear models procedure (GLM) of the Statistical Analysis System (SAS Institute, Cary, N.C.) with a split-plot model design where tissue zone represented a subplot within table beet entries, which were considered whole plots. Red and yellow entries were analyzed separately. Means comparisons were made using least significant differences (LSD). Correlations were obtained from the correlation procedure (CORR) in SAS and were calculated on an entry mean basis.

Effect of tissue zone and cycle of selection on pigment concentration in yellow table beet. BX concentration in the outer zone increased significantly over every cycle of selection except between C2-C3 as listed in Table 4, which lists the pigment distribution in five tissues zones in selected cycles of the yellow beets. BX increased in middle, center, petiole and leaf tissues over each cycle, however, these increases were not significant for every cycle of selection. The average gain per cycle between C0-C3 was 32.8, 18.1, 20.0, 37.0, and 15.0% for outer, middle, center, petiole, and leaf tissue zones, respectively. These increases are substantially higher than those achieved between C1-C3 for red table beets. This may be due to differences in selection intensity or genetic composition within the initial yellow beet populations versus the initiation populations for the red table beet populations. The initial yellow beet populations came from a cross of a red beet with high BX from the HPLS population and 'Burpee's Golden', which has a very low BX concentration. Net increases in BX were 131, 72, 80, 148, and 60% between C0-C3 in outer, middle, center, petiole and leaf zones, respectively. The greatest change in BX levels over cycles of selection was in the outer tissue zone (46.63 mg·100 $g^{-1}$ fw). BC levels were substantially lower than BX levels. BC increased over cycles of selection in all tissue zones with the greatest change in BC between C0-C3 occurring in the outer tissue zone (1.69 mg·100 $g^{-1}$ fw).

Effect of tissue zone and cycles of selection on TDS in yellow table beet. TDS levels in the outer zone were 11.0 and 13.2% higher than middle and center tissue zones, respectively. TDS levels in the outer tissue zone significantly (P>0.05) increased over cycles of selection except between C1-C2 where TDS decreased, as shown in Table 5 which contains the values of total dissolved solids in three tissue zones over cycles in the yellow beets. TDS levels in middle and center tissue zones increased over cycles of selection, however, increases were not significant for every cycle of selection. The average gain per cycle was 5.1, 4.1, and 4.7% for outer, middle and center tissue zones, respectively. The greatest increase in TDS between C0-C3 occurred in the outer tissue zone (2.22%).

Effect of planting date on pigment concentration and TDS in yellow table beet. Average BX levels of most tissue zones increased in the later planting date (Table 2), with the exception of average BX levels in the outer tissue zone, which decreased with the later planting date. Average BX was 9, 16, 14, and 37% higher in middle, center, petiole, and leaf tissue zones from the second planting date compared to tissue zones from the early planting date. Although these data are generally consistent with previous experiments (Watson and Gabelman 1982; Nilsson 1973), decreased temperatures cannot explain the increase in BX at the later planting date as has been the explanation for these results in previous studies.

TDS levels were consistently lower in beets from the second harvest date than the first, however, all TDS differences between planting dates were non-significant.

Correlations among root weight, TDS and pigment concentration in yellow table beet. Phenotypic correlations reveal a significant relationship between BC, BX, and TDS levels at both planting dates as shown in Table 3, which shows the mean squares from the analysis of pigment distribution and total dissolved solids in the yellow beets. The correlation between BC and BX was highly positive at both planting dates with r=0.80 for the late planting date. Correlations between TDS and BC or BX were also positive and ranged from r=0.52 to r=0.63 for both populations at both planting dates. The relationship between root weight and BX was significant in the late planting date (r=0.34). A negative relationship also exists between root weight and TDS with a more significant correlation present at the early planting date. These inconsistencies between planting dates may be due to differences in root weight between populations and planting dates.

Conclusions. Simple phenotypic selection has led to significant improvement of the yellow table beet populations. Specifically, the selection technique has led to a direct increase in pigment concentration in all tissue zones. Selection in the outer zone has also led to a correlated response to selection in leaf and petiole tissues in the yellow table beet populations. Rates of gain in red table beet populations have not plateaued suggesting that alleles that control pigment concentration have not been fixed and further improvement is achievable. Increased pigment concentration resulting from a correlated response to selection suggests that the entire table beet (root, leaf and petiole) could be utilized in commercial applications such as a food colorant or possibly health supplements.

It is unknown whether utilizing selection in all areas of the root would make the selection process more effective and result in roots with more uniform pigment distribution. Rates of gain were higher in the middle and center zone than the outer zone of the red populations using the current strategy illustrating the effectiveness of the current selection strategy to increase pigment concentration throughout the beet plant. In addition, differential pigment concentration throughout the root occurs across populations that are not subjected to pigment selection in the outer region such as 'Big Red' and 'Golden Boy' therefore whole root selection may not provide a significantly more effective means of increasing whole root pigmentation than the current strategy. This is confirmed by the fact that the contribution of each tissue zone to pigment concentration of the whole table beet has remained consistent throughout cycles of selection. Spatial distribution data confirm previous observations that pigment concentration is highest in outer tissue zones. The mechanism behind this phenomenon could range from simple biological to biochemical reasons involving the cell growth pattern of cambial rings or the accumulation of pigment and activation of pigment biosynthetic enzymes in cells nearer to sources of stress.

FIG. 1 illustrates the gains made in pigment amounts in the yellow beet program. This graph illustrates the response to selection across all five tissue zones over the cycles of selection for increased pigment in generations C0 to C3 of the yellow beet program. The chart marked A shows gains in betaxanthin as a percent of the corresponding concentration in C0. The chart labeled B shows the gains in betacyanin content in the beets as a percent of the amounts in the C0 generation. Note that betaxanthin levels were increased by over 100% and that betacyanins did increases as well, although the beets appeared visually yellow. The betaxanthin concentrations were over 100 mg per 100 g fresh weight for each of the yellow beet populations. This compares favorable to the existing yellow beet variety, "Burpee's Golden" which has a betaxanthin pigment concentration of about 35 mg per 100 gram fresh weight. These date make it clear that it is possible to greatly enhance the betaxanthin concentration in yellow beets while maintaining the yellow color.

Following the work described above, another year of filed planting has continued the evolution of the high pigment golden beet. For the planting season of 2005, plantings of seven accessions of populations of golden beets were made followed by analysis of the resulting beet roots for pigment concentration. These plants averaged 130.63 milligrams of betaxanthins per 100 grams of fresh weight, with a standard deviation of 30.18. This demonstrates that the desired levels of more than 100 mg of betaxanthin per 100 g fresh weight is a statistical fact for the current plant populations. The beets also continue to be golden or yellow indicating lack of predominant betacyanin content.

Seed from representative samples of the high pigment yellow beet has been placed on deposit on Jan. 4, 2007 with the American type Culture Collection (ATCC), 10801 University Boulevard, Manassas, Va. 20110-2209, USA, and has been accorded accession number PTA-8109. The deposit contains a collection of seeds from approximately sixty plants of half-sib families generated by crossing Ruby Lake and Burpee's Golden.

TABLE 1

| Color | Cycle or check cultivar | Selected year | Population |
|---|---|---|---|
| Red | C2 | 1983 | HPHS |
|  | C2 | 1983 | HPLS |
|  | C4 | 1990 | HPHS |
|  | C4 | 1990 | HPLS |
|  | C8 | 1994 | HPHS |
|  | C8 | 1994 | HPLS |
|  | C9 | 1995 | HPHS |
|  | C9 | 1995 | HPLS |
|  | C12 | 1998 | HPHS |
|  | C12 | 1998 | HPLS |
|  | C13 | 1999 | Ruby Lake |
|  | C15 | 2001 | Ruby Lake |
|  | 'Big Red' | NA[z] |  |
| Yellow | C0 | 1998 |  |
|  | C1 | 1999 |  |
|  | C2 | 2000 |  |
|  | C3 | 2001 |  |
|  | 'Golden Boy' | NA |  |

TABLE 2

| | | Pigment Concentration (mg pigment · 100 $g^{-1}$ fw) | | | | | | | | | |
|---|---|---|---|---|---|---|---|---|---|---|---|
| | Planting | Betacyanin | | | | | Betaxanhin | | | | |
| Color | Date | Outer[z] | Middle | Center | Petiole | Leaf | Outer | Middle | Center | Petiole | Leaf |
| Yellow | Early | 1.56 | 0.85 | 0.77 | 0.81 | 0.84 | 59.02 | 23.57 | 21.90 | 12.52 | 6.82 |
|  | Late | 2.08 | 1.73 | 1.60 | 0.58 | 0.99 | 52.87 | 25.62 | 25.37 | 14.24 | 9.34 |
|  | LSD 0.05 | 0.26 | 0.21 | 0.23 | 0.07 | 0.14 | 4.56 | 1.70 | 2.97 | 2.21 | 1.80 |
|  | LSD 0.01 | 0.37 | 0.29 | 0.32 | 0.10 | 0.20 | 6.31 | 2.35 | 4.10 | 3.06 | 2.49 |

TABLE 3

| Trait | Planting Date | Root weight (g) | Yellow BC | BX |
|---|---|---|---|---|
| BC | Early | −0.19 | | |
| | Late | −0.17 | | |
| BX | Early | −0.20 | 0.79** | |
| | Late | −0.34** | 0.80** | |
| TDS | Early | −0.55** | 0.63** | 0.63** |
| | Late | −0.26* | 0.54** | 0.52** |

TABLE 4

| | Pigment Concentration (mg pigment · 100 g$^{-1}$ fw) | | | | | | | | | |
|---|---|---|---|---|---|---|---|---|---|---|
| | Betacyanin | | | | | Betaxanthin | | | | |
| Entry | Outer$^z$ | Middle | Center | Petiole | Leaf | Outer | Middle | Center | Petiole | Leaf |
| C0 | 1.06 | 0.94 | 0.79 | 0.54 | 0.91 | 35.53 | 18.77 | 18.02 | 7.99 | 6.62 |
| C1 | 1.89 | 1.46 | 1.42 | 0.71 | 0.94 | 53.27 | 22.56 | 22.09 | 13.99 | 7.47 |
| C2 | 2.28 | 1.42 | 1.22 | 0.84 | 0.87 | 78.41 | 29.82 | 27.42 | 19.62 | 9.25 |
| C3 | 2.75 | 1.69 | 1.69 | 0.84 | 0.89 | 82.16 | 32.36 | 32.41 | 19.82 | 10.61 |
| Check$^y$ | 1.1 | 0.94 | 0.82 | 0.54 | 0.95 | 30.35 | 19.47 | 18.22 | 5.49 | 6.45 |
| LSD 0.05 | 0.34 | 0.53 | 0.39 | 0.11 | 0.23 | 10.63 | 4.49 | 5.86 | 3.19 | 2.18 |
| LSD 0.01 | 0.54 | 0.74 | 0.55 | 0.15 | 0.33 | 14.91 | 6.29 | 8.21 | 4.47 | 3.06 |

TABLE 5

| | Total dissolved solids (%) | | |
|---|---|---|---|
| Entry | Outer$^z$ | Middle | Center |
| C0 | 10.89 | 10.14 | 9.76 |
| C1 | 12.45 | 10.8 | 10.86 |
| C2 | 12.19 | 11.26 | 10.74 |
| C3 | 13.11 | 11.82 | 11.61 |
| 'Golden Boy' | 10.24 | 9.06 | 9.0 |
| LSD 0.05 | 0.91 | 0.97 | 1.07 |
| LSD 0.01 | 1.28 | 1.37 | 1.49 |

TABLE 6

| | Burpee's | UW Golden | 2$^{nd}$ Gold population |
|---|---|---|---|
| Mean betaxanthin content (mg/100 g fw) | 37.37 ± ? | 72.2 ± 9 | 122.2 ± 10.8 |
| Range of betaxanthin content (mg/100 g fw) | 29.2-60 | 58.9-78.1 | 104.3-137.5 |

REFERENCES CITED FOR METHODS USED

Nilsson, T. 1973. The pigment content in beetroot with regard to cultivar, growth, development and growing conditions. *Swed. J. Agr. Res.* 3:187-200.

Watson, J. F. and W. H. Gabelman. 1984. Genetic analysis of betacyanin, betaxanthine, and sucrose concentrations in roots of table beet *J. Am. Soc. Hort. Sci.* 109:386-391.

Wolyn, D. J. and W. H. Gabelman. 1990. Selection for betalain pigment concentrations and total dissolved solids in red table beets. J. Amer. Soc. Hort. Sci. 115:165-169.

We claim:

1. A beet plant comprising a yellow beet, the beet comprising at least 100 mg betaxanthins per 100 grams fresh weight when measured from the outer 2 cm of the root tissue and less betacyanin than betaxanthin.

2. A beet seed produced from the beet plant of claim 1.

3. Leaves of the beet plant of claim 1.

4. A beet root from the beet plant of claim 1.

5. The beet plant of claim 1, wherein the beet plant is grown from seed deposited as ATCC Accession No. PTA-8109.

6. A beet root from the beet plant of claim 5.

7. A beet seed produced from the beet plant of claim 5.

8. A method of producing a yellow beet comprising at least 100 mg betaxanthins per 100 grams fresh weight when measured from the outer 2 cm of the root tissue, the method comprising the steps of
   a) crossing a yellow beet population with a maintainer yellow beet population;
   b) harvesting the seed from the cross of step (a);
   c) growing the harvested seed to produce beet plants, roots and seeds; and
   d) selecting beet seeds for subsequent breeding based on a selection of high levels of betaxanthins until a level of at least 100 mg per 100 g fresh weight in the outer 2 cm of the root tissue is obtained.

9. The method of claim 8 wherein the method is repeated for at least 5 generations.

* * * * *